United States Patent [19]

Eckes et al.

[11] 4,323,675
[45] Apr. 6, 1982

[54] NOVEL STILBENE COMPOUNDS: PROCESS FOR THEIR MANUFACTURE AND THEIR USE AS OPTICAL BRIGHTENERS

[75] Inventors: Helmut Eckes; Rüdiger Erckel, both of Eppstein; Thomas Martini; Günter Rösch, both of Bad Soden am Taunus, all of Fed. Rep. of Germany

[73] Assignee: Hoechst Aktiengesellschaft, Frankfurt, Fed. Rep. of Germany

[21] Appl. No.: 162,930

[22] Filed: Jun. 25, 1980

[30] Foreign Application Priority Data

Jun. 29, 1979 [DE] Fed. Rep. of Germany ....... 2926234

[51] Int. Cl.³ .................. C07D 401/14; C07D 413/10; C07D 413/14
[52] U.S. Cl. .................................. 542/463; 542/435; 252/301.22; 252/301.24
[58] Field of Search ....................... 542/435, 462, 463

[56] References Cited

U.S. PATENT DOCUMENTS 3,759,900 9/1973 Horstmann ......................... 542/462
3,830,848 8/1974 Siegrist ............................... 542/463
4,014,871 3/1977 Kormany et al. ................... 542/462
4,113,937 9/1978 Siegrist et al. ...................... 542/462
4,138,552 2/1979 Schlapfer-Illi ...................... 542/462

FOREIGN PATENT DOCUMENTS 6171 1/1979 European Pat. Off. ............ 542/462

*Primary Examiner*—Arthur P. Demers
*Attorney, Agent, or Firm*—Connolly and Hutz

[57] ABSTRACT

Triazolyl stilbene compounds of the formula

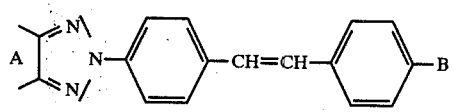

wherein A is a benzene or naphthalene ring optionally substituted by non-chromophoric substituents and B is a substituted 1,2,4-oxdiazole (3) or 1,3,5-oxdiazole (2) group, as well as a procedure for their manufacture and their use as optical brighteners.

5 Claims, No Drawings

NOVEL STILBENE COMPOUNDS: PROCESS FOR THEIR MANUFACTURE AND THEIR USE AS OPTICAL BRIGHTENERS

Subject of the present invention are 4-triazolyl stilbene compounds with improved brightening properties of the general formula 1

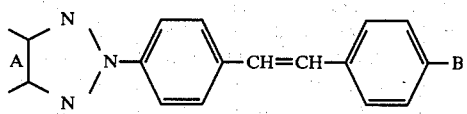

wherein A is a benzene or naphthalene ring optionally substituted by non-chromophoric substituents, B is a group of the formulae

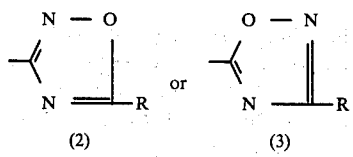

and R is a straight-chain or branched alkyl group with 1-18 C-atoms, preferably 1-6 C-atoms, which can be substituted by hydroxyl groups, halogen atoms, lower alkoxy, dialkylamino, lower alkylmercapto, chloroaryloxy, aryloxy, arylmercapto or aryl groups, in the case of R being dialkylaminoalkyl, the two alkyl groups may also form together a morpholine, piperidine or piperazine ring, or R is a group of the formula —$(CH_2CH_2O)_n$—$R^1$ with n being 1,2 or 3 and $R^1$ being H, lower alkyl or R is dialkylaminoalkoxyalkyl or alkylthioalkoxyalkyl, the alkyl groups in dialkylaminoalkoxyalkyl forming optionally together a piperidine, pyrrolidine, hexamethylenimine, morpholine or piperazine ring, or R is a group of the formula

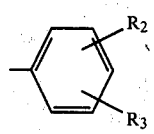

wherein $R_2$ and $R_3$ are identical or different and selected from the group consisting of hydrogen, fluorine or chlorine atoms, phenyl, lower alkyl, lower alkoxy, $(C_1-C_4)$acylamino groups or optionally modified carboxy or sulfo groups, two adjacent radicals $R_4$ and $R_5$ optionally forming together a lower alkyl group, a fused benzene ring or a 1,3-dioxapropylene group.

Suitable non-chromophoric substituents in the nucleus A are, for example, $(C_1-C_4)$-alkyl, halogen, $(C_1-C_4)$-alkoxy, cyano, carboxy and phenylsulfonyl.

Of special interest are the compounds of the formula 1, in which A and B have the abovementioned meanings and R means the following groups: $(C_1-C_6)$-alkyl, $(C_1-C_6)$-chloroalkyl, dimethyl- or diethylamino-$(C_1-C_4)$-alkyl, morpholinoethyl, N-β-piperidinoethyl, N-β-(N'-methylpiperazino)-ethyl, benzene, phenoxy-$(C_1-C_4)$-alkyl, chlorophenoxy-$(C_1-C_4)$-alkyl, $(C_1-C_4)$-alkylmercapto-$(C_1-C_4)$-alkyl, phenylmercapto-$(C_1-C_4)$-alkyl, phenyl, $(C_1-C_6)$-alkylphenyl, di-$(C_1-C_6)$-alkoxyphenyl α- or β-naphthyl or a group of the formula —$(CH_2CH_2O)_n$—$R^1$, wherein n is 1,2 or 3 and $R^1$ is a hydrogen atom or a $(C_1-C_7)$-alkyl group.

Preference is also given to the compounds of the general formula 1, wherein R in the group B is $(C_1-C_6)$-alkyl, $(C_1-C_6)$-chloroalkyl, $(C_1-C_4)$-alkoxy-$(C_1-C_4)$-alkyl, hydroxy-$(C_1-C_4)$-alkyl or a group of the formula —$(CH_2—CH_2O)_n$—R', wherein n is 2 or 3 and R' is a hydrogen atom or $(C_1-C_4)$-alkyl.

Compounds of the general formula 1, wherein A is a group of the formula

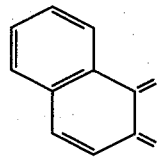

and B is a group of the formula

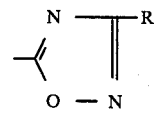

wherein R means $(C_1-C_4)$-alkyl, $(C_1-C_4)$-chloroalkyl, hydroxy-$(C_1-C_4)$-alkyl and $(C_1-C_4)$-alkoxyalkyl, are specially suitable.

R may stand for the following groups: methyl, ethyl, n- or i-propyl, n- or i-butyl, pentyl, hexyl or the chloroalkyl, hydroxyalkyl, dimethylaminoalkyl, diethylaminoalkyl, methoxyalkyl, ethoxyalkyl, propoxyalkyl, butoxyalkyl, methylmercaptoalkyl, ethylmercaptoalkyl, chlorophenoxyalkyl, phenoxyalkyl, phenylmercaptoalkyl, phenylalkyl, naphthylalkyl groups derived therefrom, or groups of the formula —$(CH_2CH_2O)$-$_n$—$R^1$, wherein n is 1,2 or 3 and $R^1$ is a hydrogen atom, a methyl, ethyl, propyl or butyl group or a dimethyl or diethylaminoalkoxyalkyl group with 1-4 C-atoms in the alkyl or alkoxy moiety or such alkylthioalkoxyalkyl groups, which also contain 1-4 C-atoms each in the individual alkyl or alkoxy moieties.

Examples hereof are the radicals of the formulae

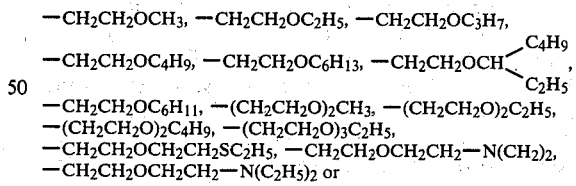

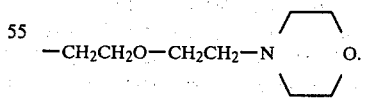

Of special importance are the following compounds:

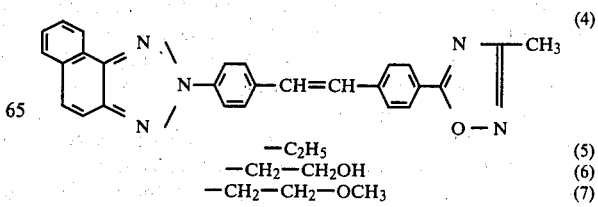

—$C_2H_5$ (5)
—$CH_2$—$CH_2OH$ (6)
—$CH_2$—$CH_2$—$OCH_3$ (7)

-continued

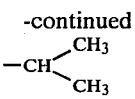 (8)

Subject of the present invention is furthermore a process for the manufacture of the compounds of the formula 1, which comprises reacting a compound of the general formula 9

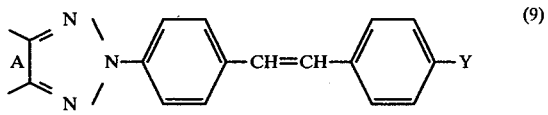 (9)

with a compound of the general formula 10

R—Z        (10)

wherein R has the aforementioned meanings and Y is a group of the formula 11

 (11)

and Z is a group of the formula 12

—COCl        (12)

or Y means a group of the formula 12 and Z is a group of the formula 11.

In the first case there are obtained compounds of the formula 1, which contain a 1,2,4-dioxazolyl-3 group and in the second case the compounds obtained contain 1,2,4-dioxazolyl-5 group. The reaction is preferably carried out in the presence of an acid-binding agent, in an inert solvent at a temperature from 20°–200° C. Suitable solvents for the reaction are, for example, chlorobenzene, dichloro- or trichlorobenzene and especially dimethylformamide, N-methylpyrrolidone, dimethylsulfoxide or nitrobenzene. Examples of acid-binding agents which can be used are sodium carbonate, potassium carbonate, calcium carbonate, triethylamine or ethyldiisopropylamine.

The compounds of the formula 9, wherein Y is a group of the formula 12, are known and described, for example, in DE-OS No. 25 39 461 and DE-OS No. 25 39 537, or they can be manufactured analogously to the known processes. The compounds of the general formula 9, wherein Y means the nitrile group, can be obtained according to the generally known processes, for example aminolysis and subsequent dehydration.

The compounds of the formula 9, wherein Y is a group of the formula 11, are obtained from the abovedescribed nitriles in known manner by reaction with hydroxylamine, preferably in alcohols or N-methylpyrrolidone.

The new compounds defined above exhibit a more or less pronounced fluorescence in a dissolved or finely dispersed state. They are therefore suitable for optically brightening the most diverse synthetic, semi-synthetic or natural organic materials or substances which contain such organic materials.

The following groups of organic materials, where optical brightening thereof is relevant, may be mentioned as examples of the above, without the survey given below being intended to express any restriction thereto:

I. Synthetic organic high-molecular materials:

(a) Polymerization products based on organic compounds containing at least one polymerizable carbon-carbon double bond, that is to say their homopolymers or copolymers as well as their after-treatment products such as, for example, crosslinking, grafting or degradation products, polymer blends or products obtained by modification of reactive groups, for example polymers based on γ,β-unsaturated carboxylic acids or derivatives of such carboxylic acids, especially on acrylic compounds (such as, for example, acrylic esters, acrylic acid, acrylonitrile, acrylamides and their derivatives or their methacrylic analogues), on olefin hydrocarbons (such as, for example, ethylene, propylene, styrenes or dienes and also so-called ABS polymers), and polymers based on vinyl and vinylidene compounds (such as, for example, vinyl chloride, vinyl alcohol and vinylidene chloride), (b) Polymerization products such as are obtainable by ring opening, for example polyamides of the polycaprolactam type, and also polymers which are obtainable both via polyaddition and via polycondensation, such as polyethers or polyacetals, (c) Polycondensation products or precondensates based on bifunctional or polyfunctional compounds possessing groups capable of undergoing condensation reactions, their homocondensation and co-condensation products, and after-treatment products, such as, for example, polyesters, especially polyesters which are saturated (for example ethylene glycol terephthalic acid polyester) or unsaturated (for example maleic acid-dialcohol polycondensates as well as their crosslinking products with copolymerizable vinyl monomers), unbranched or branched polyesters (also including those based on polyhydric alcohols, such as, for example alkyd resins), polyamides (for example hexamethylenediamine adipate), maleate resins, melamine resins, their precondensates and analogues, polycarbonates and silicones, and (d) Polyaddition products such as polyurethanes (crosslinked and non-crosslinked) and epoxide resins.

II. Semi-synthetic organic materials, for example cellulose esters of different degrees of esterification (the so-called 2½ acetate, triacetate) or cellulose ethers, regenerated cellulose (viscose, cupper ammonia cellulose) or their after-treatment products, casein plastics.

III. Natural organic materials of animal or vegetable origin, for example those based on cellulose or proteins such as cotton, wool, linen, silk, natural lacquer resins, starch, casein.

The organic materials to be optically brightened can be in the most diverse states of processing (raw materials, semi-finished goods or finished goods). On the other hand they can be in the form of structures of the most diverse shapes, that is to sy, for example, predominantly three-dimensional bodies such as slabs, profiles, injection moldings, various machined articles, chips, granules or foams, and also as predominantly two-dimensional bodies such as films, sheets, lacquers, coverings, impregnations and coatings, or as predominantly one-dimensional bodies such as filaments, fibers, flock and wires. The said materials can, on the other hand, also be in unshaped condition, in the most diverse homogeneous or inhomogeneous forms of division, such as, for example, in the form of powders, solutions, emulsions, dispersions, latices, pastes or waxes.

Fiber materials can, for example, be in the form of continuous filaments (stretched or unstretched), staple fibers, flocks, hanks, textile filaments, yarns, threads, fiber fleeces, felts, waddings, flocked structures or woven textile fabrics, textile laminates, knitted fabrics and papers, cardboards of paper pulps.

The compounds to be used according to the invention are of importance, inter alia, for the treatment of organic textile materials, especially woven textile fabrics. Where fibers, which can be in the form of staple fibers or continuous filaments or in the form of hanks, woven fabrics, knitted fabrics, fleeces, flocked substrates or laminates, are to be optically brightened according to the invention, this is advantageously effected in an aqueous medium wherein the compounds in quenstion are present in a finely divided form (suspensions, so-called microdispersions or possibly solutions). If desired, dispersing agents, stabilizers, wetting agents and further auxiliaries can be added during the treatment.

Depending on the type of brighteners used, it may be advantageous, to effect the treatment in a neutral or alkaline or acid bath. Usually, the treatment is carried out at a temperature of about 20° to 140° C., for example at the boiling point of the bath or near to this temperature (at about 90° C.). For the brightening of the textile substrates according to the invention, there can also be used solutions or emulsions in organic solvents, for example in the manner usual in the so-called solvent dyeing (padding thermofixation application, exhaustion dyeing in dyeing-machines).

The new optical brighteners according to the present invention can be added to, or incorporated in, the materials before or during their shaping. Thus they can, for example, be added to the compression molding composition or injection molding composition during the manufacture of films, sheets (for example, hot milling into polyvinyl chloride) or moldings.

Where fully synthetic or semi-synthetic organic materials are being shaped by spinning processes or via spinning compositions, the optical brighteners can be applied in accordance with the following processes:

Addition to the starting substances (for example monomers) or intermediates (for example precondensates or prepolymers), that is to say before or during the polymerization, polycondensation or polyaddition, Powdering onto polymer chips or granules for spinning compositions, Bath dyeing of polymer chips or granules for spinning compositions, Metered addition to spinning melts or spinning solutions, and Application to the tow before stretching.

The new optical brighteners according to the present invention can, for example, also be employed in the following use forms:

(a) Mixed with dyestuffs (shading) or pigments (colored pigments or especially, for example, white pigments), or as an additive to dye baths, printing pastes, discharge pastes or reserve pastes, or for the after-treatment of dyeings, prints or discharge prints.

(b) Mixed with so-called "carriers", wetting agents, plasticizers, swelling agents, anti-oxidants, light stabilizers, heat stabilizers and chemical bleaching agents (chlorite bleach or bleaching bath additives).

(c) Mixed with crosslinking agents or finishing agents (for example starch or synthetic finishes), and in combination with the most diverse textile finishing processes, especially synthetic resin finishes (for example crease-proof finishes such as "wash-and-wear", "permanent-press" or "no-iron"), as well as flameproof finishes, soft handle finishes, anti-soiling finishes or anti-static finishes, or antimicrobial finishes.

(d) Incorporation of the optical brighteners into polymeric carriers (polymerization, polycondensation or polyaddition products), in a dissolved or dispersed form, for use, for example, in coating agents, impregnating agents or binders (solutions, dispersions and emulsions) for textiles, fleeces, paper and leather, (e) as additives to so-called "master-batches", (f) as additives to the most different industrial products, to make them more marketable (for example aspect improvements or soaps, detergents, pigments), (g) in combination with other optically brightening substances, (h) in spinning-bath preparations, that is, as additives to spinning-baths, as are used for the improvement of the sliding-properties, for the further processing of synthetic fibers or from a special bath prior to the drawing of the fibers, (i) as scintillators for various purposes of a photographic nature, such as, for example, for electrophotographic reproduction or supersensitization.

(k) Depending on the degree of substitution, as laser dyestuffs. If the brightening process is combined with treatment or finishing processes, it is advantageously carried out with the aid of suitable staple products, which contain the optically brightening compounds in such as concentration that the desired brightening effect is obtained.

In certain cases the brighteners obtain their full effect by an after-treatment, for example, chemical treatment with acids, a thermal treatment or a combined chemical/thermal treatment. The optical brightening of a series of fiber substrates, for example, polyester fibers, with the brighteners according to the invention, is advisably carried out by impregnating these fibers with the aqueous dispersions at a temperature below 75° C., for example at room temperature, and by exposing them to a dry heat treatment at a temperature of more than 100° C., this heat treatment being suitably proceeded by a drying process at a moderately increased temperature, for example of at least 60° C. to about 130° C. The heat treatment in dry state is then advantageously effected by heating in a dry chamber, by ironing at the indicated temperature interval or also by a treatment with dry, overheated steam. Drying and the dry heat treatment can also be performed immediately one after the other or they can be combined in a single process.

The amount of the new optical brighteners to be used according to the invention, relative to the material to be optically brightened, can vary within wide limits. A distinct and durable effect is already achievable with very small amounts, in certain cases, for example, amounts of 0.001 percent by weight. However, amounts of up to 0.8 percent by weight and optionally of up to about 2 percent by weight can also be employed. For most practical purposes, amounts between 0.005 and 2, preferably 0.1 to 0.5, percent by weight are of interest.

For various reasons it is recommendable not to employ the brighteners as such, that is in a pure state, but mixed with the most different auxiliaries and extenders, for example anhydrous sodium sulfate, sodiumsulfate decahydrate, sodium chloride, sodium carbonate, alkali metal phosphates, such as sodium or potassium orthophosphate, sodium or potassium pyrophosphate and sodium or potassium tripolyphosphate or alkali metal silicates.

The new optical brighteners are especially suitable as additives for washing-baths or as industrial or household detergents, whereto they can be added in different manner. To washing-baths they are suitably added in the form of their solutions in water or organic solvents or in finely divided state as aqueous dispersions. To household or industrial detergents they are advantageously added in any phase of the manufacturing process of the detergent, for example to the so-called "slurry" prior to pulverizing the detergents or during the preparation of liquid detergent combinations. The compounds may be added as a solution or dispersion in water or in other solvents or without any auxiliaries as dry brightening powder. The brighteners can, for example, be mixed, kneaded or ground with the active detergent substances and be subsequently mixed with the finished washing-powder. They can, however, also be sprayed onto the finished detergent in dissolved or predispersed state.

The known mixtures of active detergent substances, for example soap in form of chips and powders, synthetics, soluble salts of sulfonic acid semi-esters of higher fatty alcohols, higher and/or poly-alkyl substituted arylsulfonic acids, sulfoncarboxylic acid esters of medium-long chain alcanols, fatty acid acyl-amino-alkyl or aminoacrylglycerine sulfonates, phosphoric acid esters of fatty alcohols and so on, can be used as detergents. Suitable builders are, for example, alkali metal poly- and alkali metal polymethaphosphates, alkali metal pyrophosphates, alkali metal salts of the carboxymethylcellulose and other "soilredeposition inhibitors", further alkali metal silicates, alkali metal carbonates, alkali metal borates, alkali metal perborates, nitrilo triacetic acid, ethylenediaminotetraacetic acid, foam stabilizers such as alkanolamides of higher fatty acids. Besides, this, the detergents can contain, for example: Antistatic agents, refattening skin protecting substances such as lanoline, enzymes, antimicrobics, perfumes and dyestuffs.

The new optical brighteners have the special advantage that they are effective even in the presence of active chlorine donors, for example hypochloride, and that they can be employed in washing-baths with ionogenic detergents, for example alkylphenolpolyglykol ethers, without significant loss of effectiveness.

The compounds according to the invention are added in amounts of 0.005–1% or more, relative to the weight of the liquid or pulverulent, finished detergent. Washing-liquors, which contain the indicated amounts of the claimed optical brighteners, confer upon textiles of cellulose fibers, polyester fibers, wool and so on, during washing, a brilliant aspect at day-light.

The washing treatment is carried out, for example, as follows:

The indicated textiles are treated for 1 to 30 minutes at 20° to 100° C. in a washing-bath which contains from 1 to 10 g/kg of a detergent and from 0.05 to 1% relative to the weight of the detergent, of the claimed brighteners. The good-to-liquor-ratio can be from 1:3 to 1:50. After washing the product is rinsed and dried as usually. The washing-bath can contain as bleaching additive 0.2 g/l of active chlorine (for example hypochlorine) or from 0.1 to 2 g/l sodiumperborate.

The following examples illustrate the invention. Percentages are given by weight; melting and boiling points are uncorrected, unless otherwise stated.

EXAMPLES

Example 1a 39.1 g of the compound 13

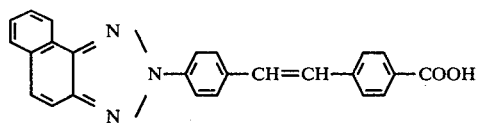

(13)

are stirred in 400 ml of xylene with 1 g dimethylformamide and 24 g thionylchloride for 5 hours while refluxing, subsequently the excess thionylchloride is distilled off, sucked off at room temperature, washed with xylene and hexane and dried. 34.8 g (85% of the theory) of the compound 14, which is employed without further purification, are obtained.

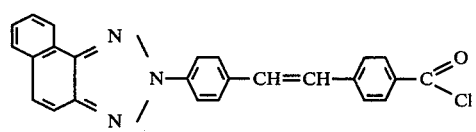

(14)

Example 1b 4.1 g of the acid chloride 14 were introduced into a solution of 1 g acetamidoxime in 40 ml dimethylformamide, for 10 minutes, the batch is stirred for 1 hour at 25° C. and subsequently for 2 hours, while refluxing. After cooling, the product is sucked off, washed with methanol and dried. 3.1 g (73% of the theory) of the compound 15

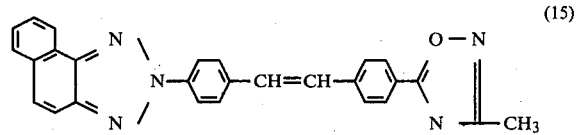

(15)

which melts after recrystallization from dimethylformamide and clarification with active carbon at 248° to 250° C., are obtained.

Absorption (measured in dimethylformamide):
$\lambda max = 377$ nmm
$\epsilon = 7.10 \times 10^4$
Fluorescence (measured in dimethylformamide):
$\lambda max = 436$ nm

Example 2

1 g propionamidoxime was added to 50 ml of toluene in conjunction with 1 g triethylamine, 4.1 g of the acid chloride 14 were added and stirring was continued for 1 hour. The product is sucked off, washed with methanol and water and dried. 4.2 g of the compound 16

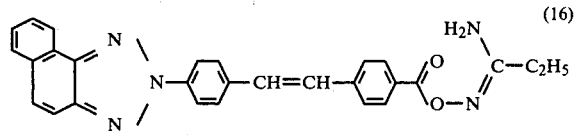

(16)

which without further purification is stirred in 40 ml N-methyl-pyrrolidine for 2 hours at 160° C., are obtained. After cooling, the product is sucked off, washed with methanol and dried. 3.1 g (70% of the theory) of the compound 17

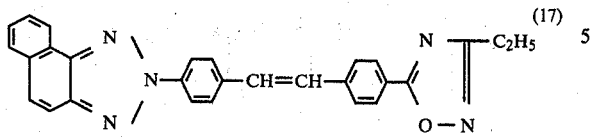

which after recrystallization from dimethylformamide and clarification with active carbon melts at 219°–220° C., are obtained.

Absorption (measured in dimethylformamide):
$\lambda max = 370$ nm
$\epsilon = 7.14 \times 10^4$ Fluorescence (measured in dimethylformamide):
$\lambda max = 437$ nm Analogously to Example 2 there are obtained the compounds of the formula 18 which are listed in the following table.

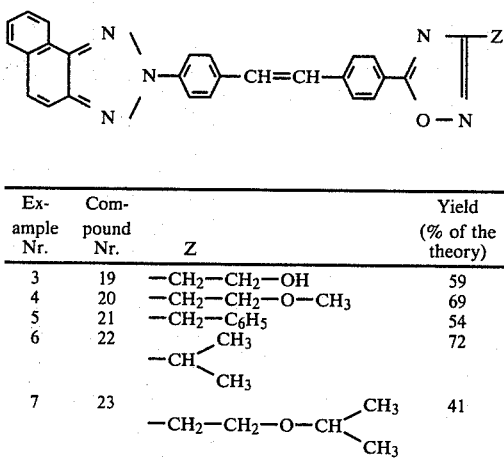

| Example Nr. | Compound Nr. | Z | Yield (% of the theory) | Fp[1] (°C.) | Absorption $\lambda max$ (nm) | $\times 10^4$ | fluorescence (measured in DMF) $\lambda max$ (nm) |
|---|---|---|---|---|---|---|---|
| 3 | 19 | —CH$_2$—CH$_2$—OH | 59 | 218–225 | 375 | 6,94 | 436 |
| 4 | 20 | —CH$_2$—CH$_2$—O—CH$_3$ | 69 | 187–197 | 375 | 6,92 | 437 |
| 5 | 21 | —CH$_2$—C$_6$H$_5$ | 54 | 258–259 | 376 | 7,34 | 438 |
| 6 | 22 | —CH(CH$_3$)$_2$ | 72 | 199–200 | 375 | 7,08 | 442 |
| 7 | 23 | —CH$_2$—CH$_2$—O—CH(CH$_3$)$_2$ | 41 | 188–231 | | | |

[1]In part, the compounds melt within a rather broad temperature range.

What is claimed is:

1. A compound of the formula

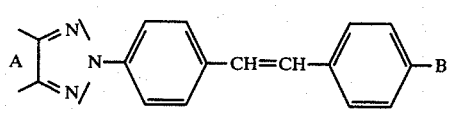

wherein A is a benzene or naphthalene ring which is unsubstituted or substituted by non-chromophoric substituents, B is a group of the formulae

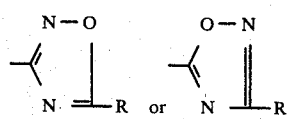

and R is a straight-chain or branched alkyl group with 1–18 C-atoms, preferably 1–6 C-atoms, which is unsubstituted or substituted by hydroxyl groups, halogen atoms, lower alkoxy, dialkylamino, lower alkylmercapto, chloroaryloxy, aryloxy, arylmercapto, aryl, morpholine, piperidine or piperazine groups, or R is a group of the formula —(CH$_2$CH$_2$O)$_n$—R$^1$ with n being 1, 2 or 3 and R$^1$ being H, lower alkyl or R is dialkylaminoalkoxyalkyl, alkylthioalkoxyalkyl, piperidine-alkoxyalkyl, hexamethylenimine-alkoxyalkyl, morpholine-alkoxyalkyl or piperazine-alkoxyalkyl or R is a group of the formula

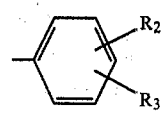

wherein R$_2$ and R$_3$ are identical or different and are selected from the group consisting of hydrogen, fluorine, chlorine, phenyl, lower alkyl, lower alkoxy, lower acylamino, or two adjacent radicals R$_4$ and R$_5$ form together a lower alkylene group, a fused benzene ring or a 1,3-dioxapropylene group.

2. Compounds of the formula 1, according to claim 1, wherein A and B have the meanings mentioned in claim 1 and R is (C$_1$–C$_6$)-alkyl, (C$_1$–C$_6$)-chloroalkyl, dimethyl- or diethylamino- (C$_1$–C$_4$)-alkyl, morpholinoethyl, N-$\beta$-piperidinoethyl, N-$\beta$-(N'-methylpiperazino)-ethyl, benzene, phenoxy-(C$_1$–C$_4$)-alkyl, chlorophenoxy-(C$_1$–C$_4$)-alkyl, (C$_1$–C$_4$)-alkylmercapto-(C$_1$–C$_4$)-alkyl, phenylmercapto-(C$_1$–C$_4$)-alkyl, phenyl, (C$_1$–C$_6$)-alkylphenyl, di-(C$_1$–C$_6$)-alkylphenyl, chlorophenyl, dichlorophenyl, (C$_1$–C$_6$)-alkoxyphenyl $\gamma$ or $\beta$-naphthyl or a group of the formula —(CH$_2$CH$_2$O)—$_n$R$^1$, wherein n is 1, 2 or 3 and R$^1$ is a hydrogen atom or a (C$_1$–C$_7$)-alkyl group.

3. Compounds of the formula 1, according to claim 1, wherein A and B have the meanings mentioned in claim 1 and R means (C$_1$–C$_6$)-alkyl, (C$_1$–C$_6$)-chloroalkyl, (C$_1$–C$_4$)-alkoxy-(C$_1$–C$_4$)-alkyl, hydroxy-(C$_1$–C$_4$)-alkyl or a group of the formula —(CH$_2$CH$_2$O)$_n$—R', wherein n is 2 or 3 and R' is a hydrogen atom or (C$_1$–C$_4$)-alkyl.

4. Compounds of the formula 1, according to claim 1, wherein A means a group of the formula

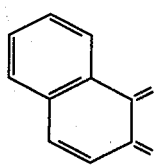

and B is a group of the formula

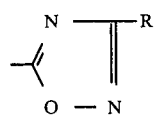
wherein R is $(C_1-C_4)$-alkyl, $(C_1-C_4)$-chloroalkyl, hydroxy-$(C_1-C_4)$-alkyl or $(C_1-C_4)$-alkoxy-$(C_1-C_4)$-alkyl.
5. Compounds of the formula 1, according to claim 1, wherein A is a group of the formula
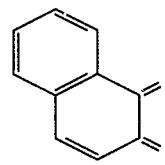
and B means a group of the formula
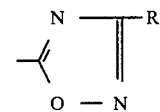
wherein R means methyl, ethyl, i-propyl, hydroxyethyl or methoxyethyl.
* * * * *